(12) United States Patent
Turner

(10) Patent No.: US 7,147,609 B2
(45) Date of Patent: Dec. 12, 2006

(54) PENILE VOLUMETRIC MEASURING DEVICE

(76) Inventor: Jason E. Turner, 5333 16th St. NW., Washington, DC (US) 20011

( * ) Notice: Subject to any disclaimer, the term of this patent is extended or adjusted under 35 U.S.C. 154(b) by 0 days.

(21) Appl. No.: 10/995,663

(22) Filed: Nov. 22, 2004

(65) Prior Publication Data
US 2006/0111650 A1    May 25, 2006

(51) Int. Cl.
*A61B 5/103* (2006.01)
*A61B 5/117* (2006.01)
*G01F 17/00* (2006.01)

(52) U.S. Cl. .......................... 600/587; 73/149
(58) Field of Classification Search ............... 600/587, 600/38, 39, 507; 73/149, 861, 861.47, 223, 73/861.49, 226
See application file for complete search history.

(56) References Cited

U.S. PATENT DOCUMENTS 2,845,060 A * 7/1958 Roman ........................ 600/485
4,338,953 A * 7/1982 Ward ........................... 600/587
4,875,488 A * 10/1989 Shimazu et al. ............. 600/507

2004/0001204 A1 * 1/2004 Boone et al. ............... 356/437

FOREIGN PATENT DOCUMENTS

FR          1426229 A   * 11/1964
WO      WO 200175404 A1 * 10/2001

OTHER PUBLICATIONS

Stanton et al., "Non-Invasive Assessment of the Lymphedematous Limb", LYMPHOLOGY, 33 (2000) 122-135.*

* cited by examiner

*Primary Examiner*—Max F. Hindenburg
*Assistant Examiner*—Jonathan Foreman
(74) *Attorney, Agent, or Firm*—John R. Ross; John R. Ross, III

(57) ABSTRACT

A volumetric measuring device for measuring a body part. The device includes a fluid container filled with fluid. The fluid container has a body part opening for permitting the insertion of a body part and a displaced fluid opening for permitting the flow of fluid that has been displaced as the result of inserting the body part. A watertight barrier covers the body part opening and maintains a watertight seal over the body part opening while the body part is being inserted. The volumetric measurement is determined by measuring the amount of displaced fluid after the insertion of the body part through the body part opening. In a preferred embodiment, the body part being measured is an erect penis.

17 Claims, 5 Drawing Sheets

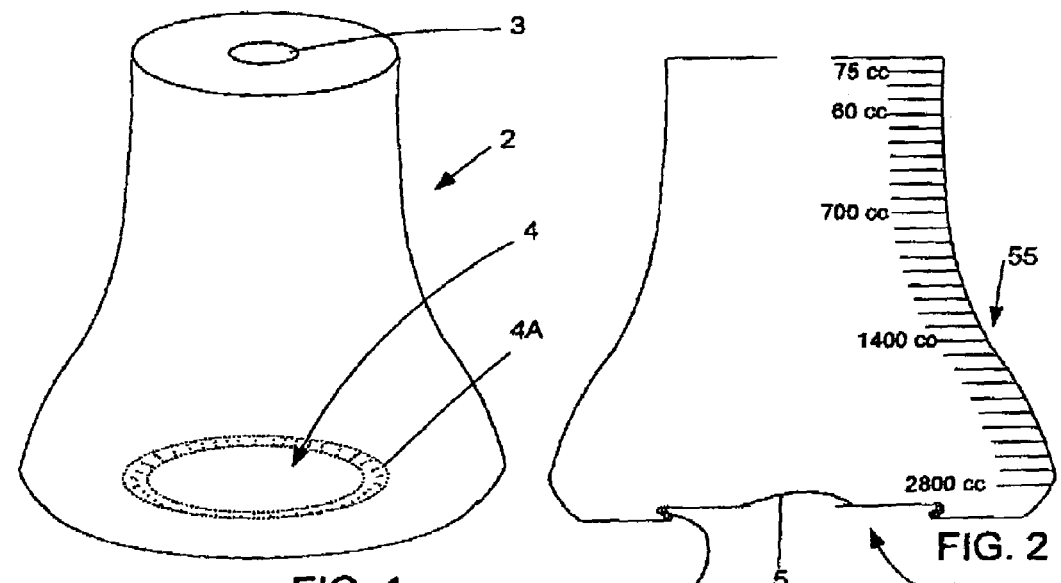
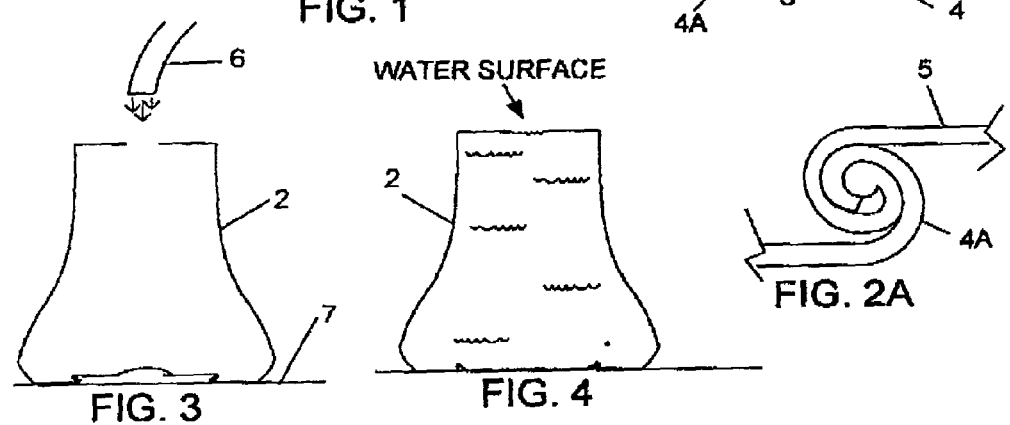
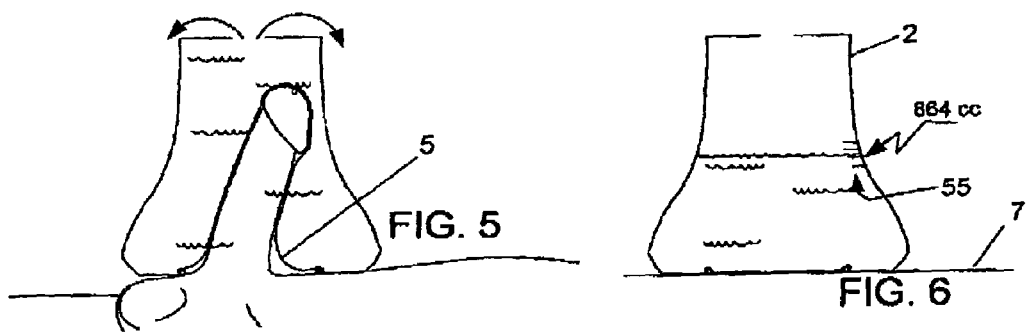

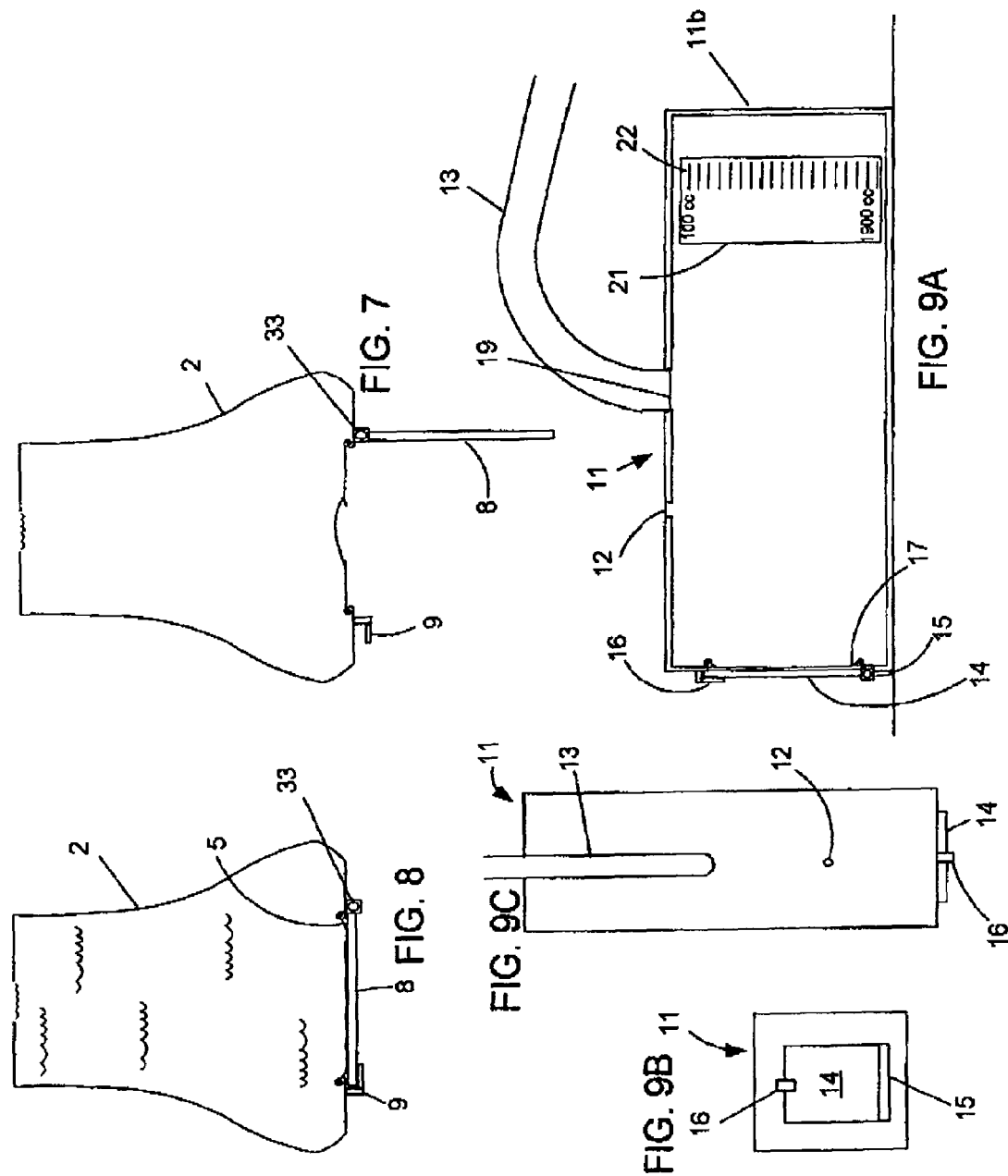

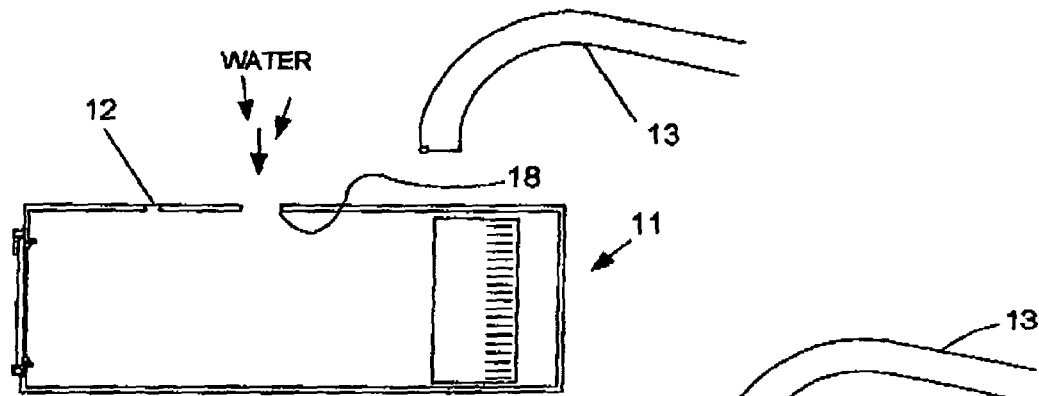
FIG. 10
FIG. 11
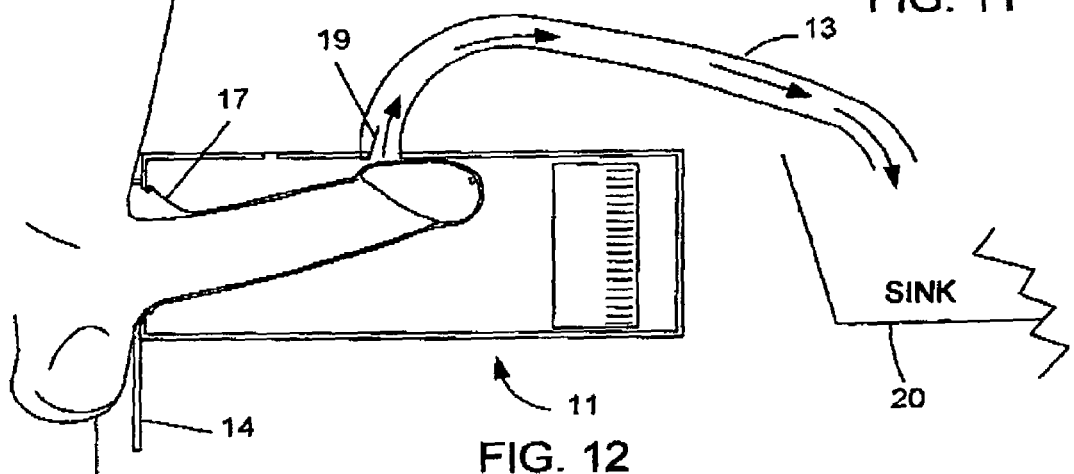
FIG. 12
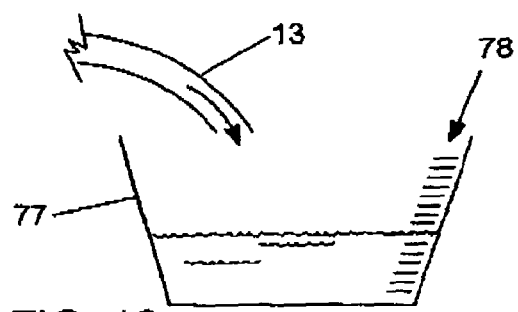
FIG. 19

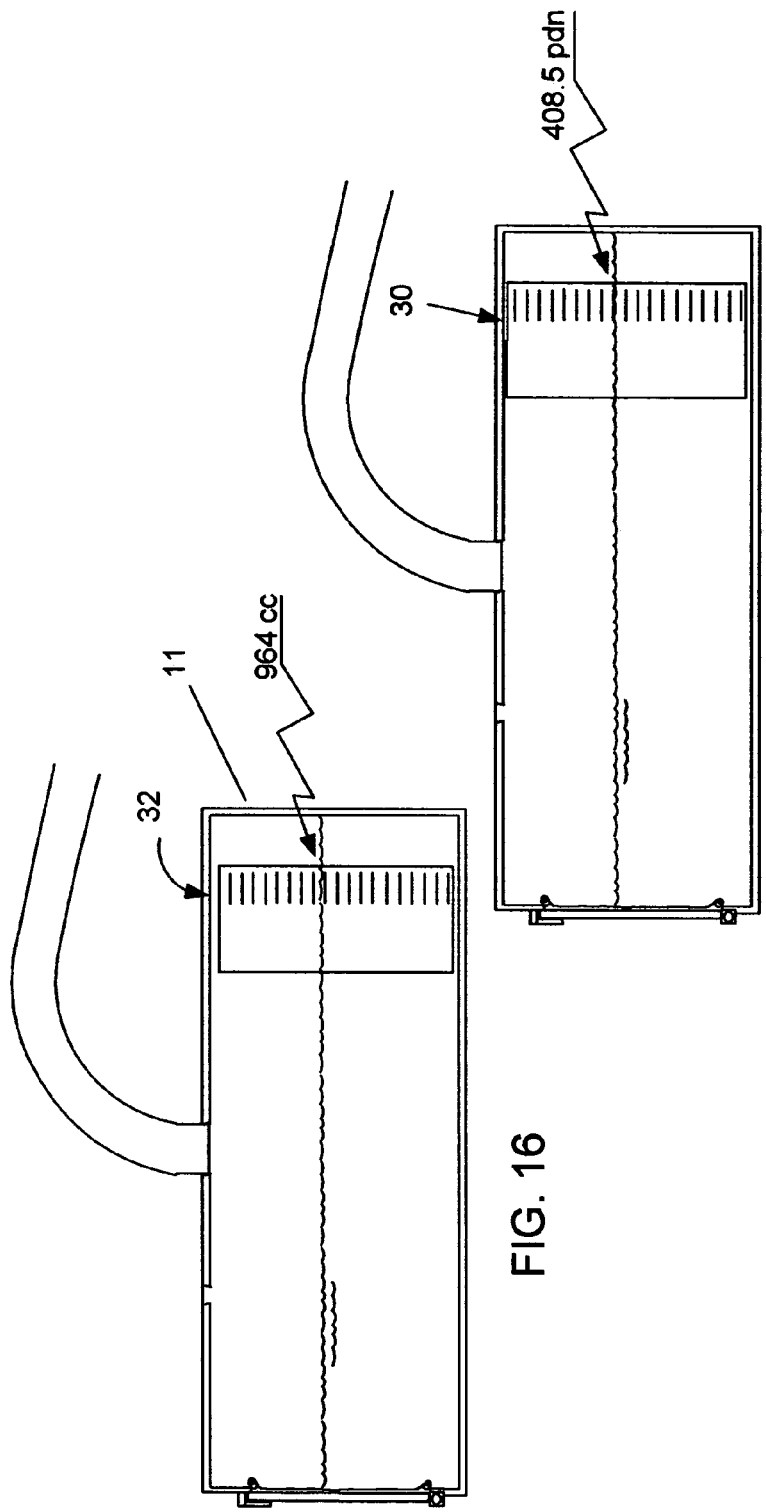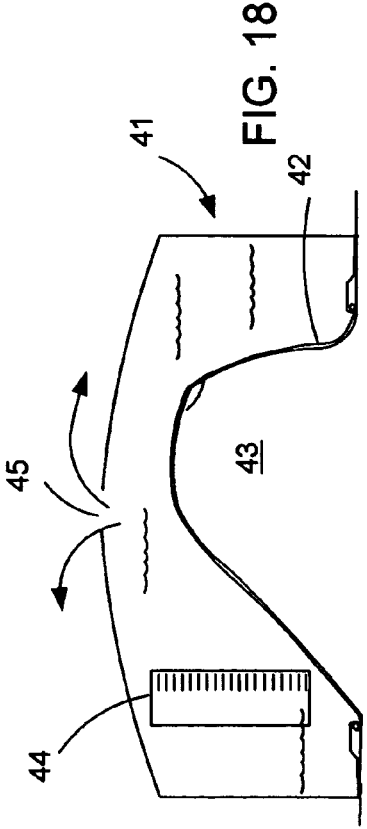

PENILE VOLUMETRIC MEASURING DEVICE

The present invention relates to measuring devices, and in particular, to measuring devices for measuring the size of an erect penis.

BACKGROUND OF THE INVENTION

Throughout history, there has been discussion and focus on the human male sex organ. Generally, having a large penis is seen as more masculine and manly than having a small penis. Well-endowed male pornography stars are looked at by many with admiration and envy due to the size of their penis.

In recent times, society has shown a strong resurgence in interest regarding matters pertaining to the penis. Viagra® (Viagra is a registered trademark of the Pfizer Corporation and refers to a compound for treating erectile dysfunction) has enjoyed tremendous success since its recent entry into the marketplace. Once marketed solely to older men having trouble achieving and maintaining an erection, Viagra® is now being marketed to and bought by younger men looking to enhance their sex lives. Moreover, just as a woman can undergo surgery for breast augmentation, so can a man undergo surgery to increase the size of his penis. The Internet is brimming with ads that market or sell products which claim to increase penis size.

With all the recent attention shown to increasing penis size, there is a remarkable lack of convenient and accurate methods for measuring the penis. Most men merely take a ruler and measure the size of their penis in inches. However, to adequately describe the size of a penis the length alone is not enough. Nor is it enough to know the diameter at an arbitrary point. The penis is not shaped like a true cylinder, but rather it has a more complicated shape. Therefore, a method for measuring the size of a penis needs to account for the unusual shape and size of the human penis.

What is needed is a better device for measuring the size of the penis.

SUMMARY OF THE INVENTION

The present invention provides a volumetric measuring device for measuring a body part. The device includes a fluid container filled with fluid. The fluid container has a body part opening for permitting the insertion of a body part and a displaced fluid opening for permitting the flow of fluid that has been displaced as the result of inserting the body part. A watertight barrier covers the body part opening and maintains a watertight seal over the body part opening while the body part is being inserted. The volumetric measurement is determined by measuring the amount of displaced fluid after the insertion of the body part through the body part opening. In a preferred embodiment, the body part being measured is an erect penis.

BRIEF DESCRIPTION OF THE DRAWINGS

FIG. 1 shows a preferred fluid container.

FIG. 2 shows a side view of a preferred embodiment of the present invention.

FIG. 2A shows a preferred watertight barrier.

FIGS. 3–6 show a preferred method for utilizing the present invention.

FIGS. 7–8 show another preferred embodiment of the present invention.

FIGS. 9A–9C show another preferred embodiment of the present invention.

FIGS. 10–14 show another preferred method for utilizing the present invention.

FIG. 16 shows another preferred embodiment of the present invention.

FIG. 17 shows another preferred embodiment of the present invention.

FIG. 18 shows another preferred embodiment of the present invention.

FIG. 19 shows another preferred embodiment of the present invention.

DETAILED DESCRIPTION OF THE PREFERRED EMBODIMENTS

First Preferred Embodiment

Preferred Fluid Container

Figure 13:
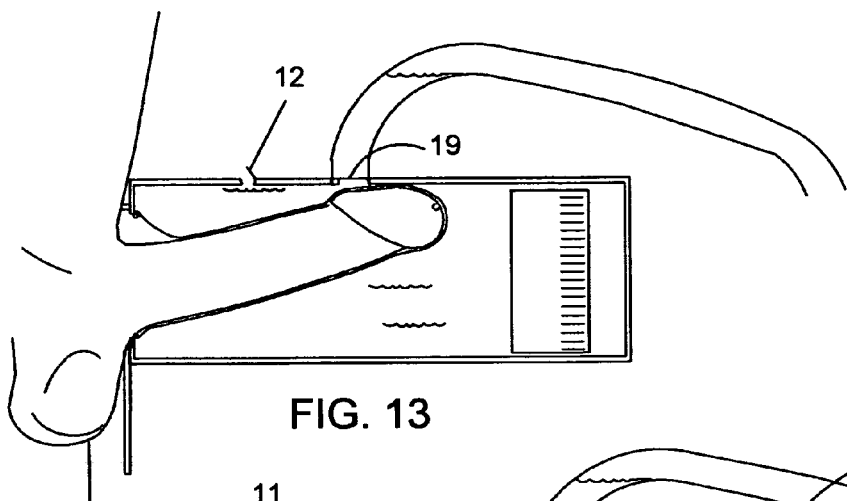

FIG. 1 shows preferred fluid container 2. Fluid container 2 has displaced fluid opening 3 and body part opening 4. Fluid container 2 preferably has a height of approximately 13 inches and a diameter near opening 3 of approximately 4 inches. The diameter towards the base of fluid container 2 near opening 4 is approximately 6 inches.

Preferred Scale

As shown in FIG. 2, fluid container 2 has scale 55 for measuring the fluid inside fluid container 2. As shown by referring to FIG. 2, fluid container 2 is capable of holding approximately 2800 cc of fluid.

Watertight Barrier

FIG. 2 also shows watertight barrier 5 stretched over body part opening 4. Watertight barrier 5 forms a watertight seal over opening 4. In a preferred embodiment, watertight barrier 5 is a latex condom. By utilizing a condom as watertight barrier 5, multiple users can each safely use the device by supplying their own personal condom. The opening of the condom fits over circular lip 4A surrounding opening 4. For example, FIG. 2A shows a detailed view of watertight barrier 5 stretched over lip 4A of opening 4 to form the watertight seal.

Utilization of a Preferred Embodiment of the Present Invention

In FIG. 3, a user is filling fluid container 2 with water from hose 6. Fluid container 2 is resting on table 7.

In FIG. 4, water has been filled to the top of fluid container 2.

In FIG. 5, a user has inserted his erect penis into fluid container 2 through opening 4 (FIG. 1) while laying on his back. As indicated by the arrows, water inside fluid container 2 is overflowing. Watertight barrier 5 stretches as it receives the erect penis. Watertight barrier 5 also retains its watertight seal over opening 4 so that no water leaks out through opening 4.

In FIG. 6, fluid container 2 has been placed back down on top of table 7. An ample portion of the fluid has spilled out through opening 3 and the surface of the water level inside fluid container 2 has dropped significantly. By referring to scale 55, the user can determine that approximately 864 cc of water poured out though opening 3 while his erect penis was inserted. Therefore the user can conclude that his penis has a volume of approximately 864 cc.

Second Preferred Embodiment

FIG. 7 shows another preferred embodiment of the present invention. In this embodiment, door 8 is attached to fluid container 2 at hinge connection 33. By utilizing door 8, a user is able to carry fluid container 2 with him while it is filled with water. For example, FIG. 8 shows door 8 latched shut against fluid container 2 at latch 9. Door 8 is supporting the weight of the water inside fluid container 2 as it exerts force on watertight barrier. When the user is ready to insert his erect penis into fluid container 2, the user opens door 8 and inserts his penis in a manner similar to that described above.

Third Preferred Embodiment

A third preferred embodiment is shown in FIGS. 9A–9C. Measuring device 11 has fluid container 11b that is preferably approximately 13 inches×3 inches×3 inches and preferably holds approximately 1900 cc of fluid. Measuring device 11 is preferably fabricated from plastic and includes see-through window 21 having scale 22.

Measuring device 11 includes hose 13 connected to its top and vent 12 also on its top. In a preferred embodiment, hose 13 is threaded onto the top of measuring device 11 and hose 13 includes valve 19. Door 14 is connected to the side via hinge 15 and is latched shut with latch 16. Door 14 covers watertight barrier 17.

Utilization of the Third Preferred Embodiment

In FIG. 10, the user has removed hose 13 from displaced fluid opening 18 of measuring device 11. Door 14 and vent 12 are closed. The user is adding water to measuring device 11 through opening 18.

In FIG. 11, the user has attached hose 13 to measuring device 11 over opening 18. The user has also opened valve 19.

In FIG. 12, the user has unlatched and then opened door 14. The user then has inserted his erect penis into measuring device 11 through the body part opening covered by watertight barrier 17. Water inside measuring device 11 is displaced by the user's erect penis and it flows out through open valve 19 and then through hose 13 into sink 20.

In FIG. 13, the user has closed valve 19 and opened vent 12. The user has opened vent 12 to break any vacuum that may result as the erect penis is removed from measuring device 11.

Figure 14:
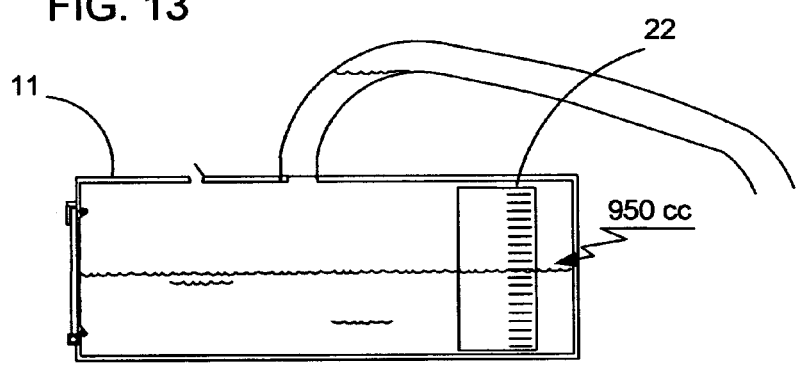

In FIG. 14, the user has removed his erect penis from measuring device 11. Water still inside hose 13 is prevented from flowing back into measuring device 11 by closed valve 19. Door 14 has been shut and latched. The water remaining inside measuring device 11 is measured on scale 22. The user determines that since 947 cc of water was displaced by his erect penis, it can therefore be concluded that his penis has a displacement of 947 cc.

Fourth Preferred Embodiment

Figure 15:
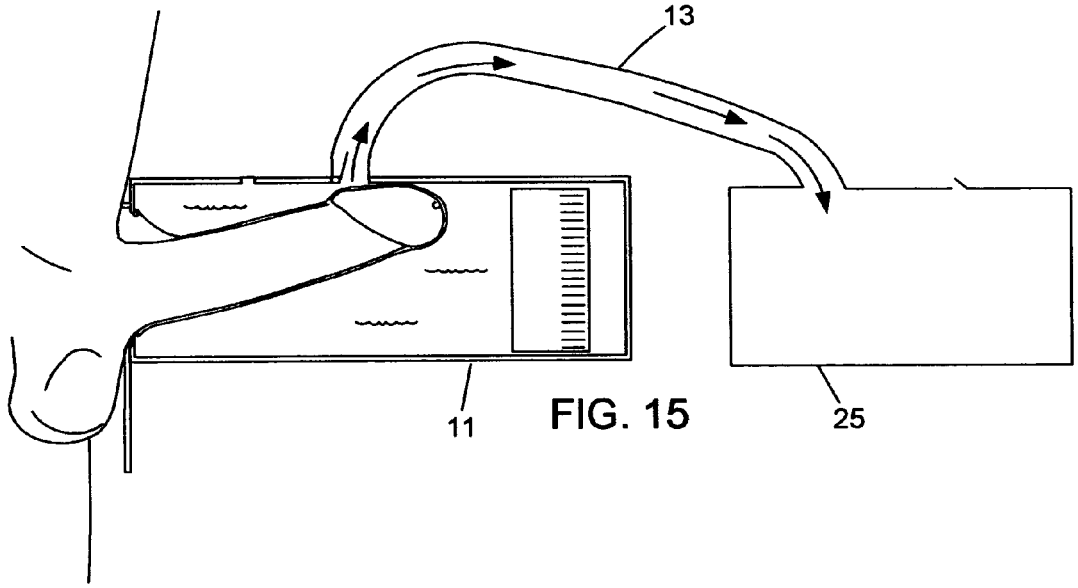
FIG. 15 shows another preferred embodiment of the present invention.

A fourth preferred embodiment of the present invention is shown in FIG. 15. The fourth preferred embodiment is very similar to the third preferred embodiment with an exception being that sink 20 (FIG. 12) has been replaced with portable fluid receptacle 25. For example, FIG. 15 shows hose 13 connected at one end to measuring device 11 and its other end connected to fluid receptacle 25. With the fourth preferred embodiment, the user does not have to be near a sink to utilize the present invention. Water displaced from measuring device 11 will be directed to fluid receptacle 25 via hose 13.

Fifth Preferred Embodiment

A fifth preferred embodiment is shown in FIG. 17. The embodiment shown in FIG. 17 is very similar to earlier preferred embodiments with an exception being that scale 30 replaced the earlier described scales.

For example, in FIG. 16 measuring device 11 utilizes scale 32 to measure the displacement of a user's erect penis. A very well endowed human male having an erect penis having length 12 inches and diameter of 2.5 inches may have an erect penis that has a volume of approximately 964 cubic centimeters. In comparison, a more typical male may have an erect penis size of approximately 6 inches and diameter of 1.75 inches. This more typical male will then have an erect penis that has a volume of approximately 236 cubic centimeters.

Applicant has noted that it is potentially confusing to compare or categorize human male penis size if the scale being utilized is cubic centimeters. Therefore, Applicant has devised his own scale which he refers to as "penile displacement number" or "pdn". Preferably, the scale is designed so that the average male has a pdn of 100. By designing the scale so that the average size penis is 100 pdn, it makes this preferred embodiment more appealing to the average user. Applicant believes that it is more of a positive reinforcement to the user to say that he has a "100 pdn" rather than saying that he has a "23 pdn" or a "24 pdn". Hence, in one embodiment, assuming that the volumetric displacement of the average erect penis is 236 cc, a preferred conversion factor between penile displacement number and cubic centimeters is 1 pdn=2.36 cc. Using this conversion factor a well-endowed male porn star having a penis volume of 964 cubic centimeters would instead refer to his erect penis as having a pdn of 408.5. Or, he might say that his penis size is 408.5 pdn. In comparison, an average male having a penis volume of 236 cubic centimeters would instead refer to his erect penis as having a pdn of 100. Or, he might say that his penis size is 100 pdn.

By utilizing the above-described preferred pdn scale, the average male is shown to have penis size equal to 100 pdn. It is then very easy to see how the average male compares to a very well endowed male. In the example above, it is immediately apparent that the male having a 408.5 pdn has a penis size that is approximately 308.5 percent above the size of the average male. Also, for example, a male with a penis size 10 percent above average could brag to his friends and lovers that he has a pdn of 110.

In FIG. 17, scale 30 is written in pdn units so that no mathematical conversion is necessary. For example by directly reading scale 30, the user can determine that the size of the erect penis is 408.5 pdn.

Sixth Preferred Embodiment

A sixth preferred embodiment is shown in FIG. 18. Although the above preferred embodiments described the utilization of the present invention to measure the size of an erect penis, the volumetric displacement of other body parts can likewise be determined with the present invention. For example, in FIG. 18 a user has inserted her breast 43 into measuring device 41. Water inside measuring device 41 is overflowing through displaced fluid opening 45. Watertight barrier 42 forms a watertight seal between the water in measuring device 41 and breast 43.

To measure the volumetric displacement of her breast, the user removes her breast from measuring device 41 and then places measuring device 41 on a flat surface. The user then refers to scale 44 to determine the amount of water displaced. The amount of water displaced is equivalent to the volumetric displacement of her breast.

Although the above-preferred embodiments have been described with specificity, persons skilled in this art will recognize that many changes to the specific embodiments disclosed above could be made without departing from the spirit of the invention. For example, although the above preferred embodiments disclosed how the present invention can be used to volumetrically measure the penis and the breast, it could also be used to measure other body parts. For example, a weight lifter might be interested in measuring the volumetric change in the size of his arm after completing a rigorous workout. The present invention could easily be configured to accommodate the size of an arm. Also, another preferred embodiment could be utilized that is similar to the embodiment shown in FIG. 12. In FIG. 19, sink 77 is portable and is sold along with measuring device 11. Sink 77 includes scale 78. Therefore, the amount of fluid displaced can be measured inside sink 77 utilizing scale 78 to determine the size of the penis. Examples of a preferred portable sink include a cup with a scale, a bowl with a scale, or a bucket with a scale. Also, although it was described how a preferred conversion factor for determining pdn is 1 pdn=2.36 cc, many other conversion factors could also be utilized. For example, another possible conversion factor is 1 pdn=10 cc. Utilizing this conversion factor, an erect penis of 964 cc would have a pdn of 96.4. Or, the conversion factor could be 1:1 so that 1 pdn=1 cc. Regardless of the conversion factor, it is Applicant's belief that by referring to the scale as measuring in units of "penile displacement number" or "pdn", a user will be more interested and more inclined to use the present invention. Also, although it was described how watertight barrier 5 is preferably a condom, watertight barrier 5 can be fabricated from a variety of other watertight materials. For example, it could be flexible rubber, flexible plastic or a flexible latex based membrane. Therefore, the attached claims and their legal equivalents should determine the scope of the invention.

What is claimed is:

1. A volumetric measuring device for measuring body parts, comprising:
   A. a fluid container filled with fluid,
   B. a body part opening for permitting the insertion of a body part,
   C. a displaced fluid opening for permitting the flow of fluid that has been displaced as a result of the insertion of said body part through said body part opening,
   D. a watertight barrier for completely covering said body part opening, wherein said watertight barrier permits the insertion of said body part and into said body part opening while simultaneously maintaining a watertight seal around said body part opening, and
   E. a door connected to said fluid container and covering said watertight barrier, wherein the volumetric measurement of said body part is determined by measuring the amount of said displaced fluid after the insertion of said body part through said body part opening.

2. The volumetric measuring device as in claim 1, wherein said body part is an erect penis.

3. The volumetric measuring device as in claim 1, wherein said body part is a human breast.

4. The volumetric measuring device as in claim 1, wherein said watertight barrier is a condom.

5. The volumetric measuring device as in claim 1, further comprising a vent attached to said fluid container.

6. The volumetric measuring device as in claim 1, wherein the volume of said displaced fluid is measured in cubic centimeters.

7. The volumetric measuring device as in claim 1, wherein said watertight barrier is a flexible latex based membrane.

8. The volumetric measuring device as in claim 1, further comprising a scale attached said fluid container.

9. The volumetric measuring device as in claim 8, wherein said scale measures in units of penile displacement number.

10. The volumetric measuring device as in claim 1, further comprising a hose connected to said fluid container at said displaced fluid opening.

11. The volumetric measuring device as in claim 10, wherein said hose directs said displaced fluid to a sink.

12. The volumetric measuring device as in claim 10, wherein said hose directs said displaced fluid to a portable fluid receptacle.

13. The volumetric measuring device as in claim 10, wherein said hose comprises a valve for preventing the backflow of said displaced fluid into said fluid container.

14. The volumetric measuring device as in claim 1, wherein the volume of said displaced fluid is measured in penile displacement number.

15. The volumetric measuring device as in claim 14, wherein 100 pdn is approximately equal to a penis having a length of approximately 6 inches and a diameter of approximately 1.75 inches.

16. The volumetric measuring device as in claim 14, wherein one said penile displacement number is approximately equal to 2.36 cubic centimeters.

17. A volumetric measuring device for measuring body parts, comprising:
   A. a fluid container filled with fluid,
   B. a body part opening for permitting the insertion of a body part,
   C. a displaced fluid opening for permitting the flow of fluid that has been displaced as a remit of the insertion of said body part through said body part opening,
   D. a watertight barrier for covering said body part opening, wherein said watertight barrier permits the insertion of said body part into said body part opening while simultaneously maintaining a watertight seal around said body part opening, and
   E. a hinged door connected to said fluid container and covering said watertight barrier, wherein the volumetric measurement of said body part is determined by measuring the amount of said displaced fluid after the insertion of said body part through said body part opening.

* * * * *